(12) United States Patent
O'Dea (10) Patent No.: US 8,521,249 B2
(45) Date of Patent: Aug. 27, 2013

(54) METHOD AND APPARATUS FOR DETERMINING VOLUME OF A VESSEL

(75) Inventor: John O'Dea, Bearna (IE)

(73) Assignee: Flip Technologies Limited, Galway (IE)

( * ) Notice: Subject to any disclaimer, the term of this patent is extended or adjusted under 35 U.S.C. 154(b) by 285 days.

(21) Appl. No.: 12/809,580

(22) PCT Filed: Dec. 22, 2008

(86) PCT No.: PCT/IE2008/000125
§ 371 (c)(1),
(2), (4) Date: Aug. 25, 2010

(87) PCT Pub. No.: WO2009/081387
PCT Pub. Date: Jul. 2, 2009

(65) Prior Publication Data
US 2010/0312181 A1    Dec. 9, 2010

(30) Foreign Application Priority Data

Dec. 20, 2007  (IE) .................................. S2007/0921
Apr. 9, 2008   (IE) .................................. S2008/0266

(51) Int. Cl.
*A61B 5/04*     (2006.01)
(52) U.S. Cl.
USPC ........... 600/373; 600/486; 600/547; 600/593; 604/96.01

(58) Field of Classification Search
USPC .................................................. 600/547, 593
See application file for complete search history.

(56) References Cited

U.S. PATENT DOCUMENTS

| | | | |
|---|---|---|---|
| 2004/0073138 A1* | 4/2004 | Greco et al. | 600/561 |
| 2008/0161730 A1* | 7/2008 | McMahon et al. | 600/593 |
| 2009/0062684 A1* | 3/2009 | Gregersen et al. | 600/547 |

FOREIGN PATENT DOCUMENTS

| | | |
|---|---|---|
| WO | 2006/002635 A1 | 1/2006 |
| WO | 2006/090351 A1 | 8/2006 |
| WO | 2007/044244 A2 | 4/2007 |
| WO | 2008/042347 A1 | 4/2008 |

* cited by examiner

*Primary Examiner* — Michael Kahelin
*Assistant Examiner* — Mitchell Alter
(74) *Attorney, Agent, or Firm* — Sughrue Mion, PLLC (57) ABSTRACT

A method and apparatus for determining the volume of a pouch formed in a stomach during bariatric surgery comprises a balloon catheter having an inflatable balloon located at a distal end of a catheter for locating in the stomach. A pair of spaced apart stimulating electrodes are located on the catheter within the balloon and a plurality of spaced apart sensing electrodes are located on the catheter between the stimulating electrodes. The balloon in the stomach is inflated by a saline solution to define the interior of the pouch. By applying a constant current signal to the stimulating electrodes, the volume of the pouch is determined from signals read from the sensing electrodes.

10 Claims, 7 Drawing Sheets

METHOD AND APPARATUS FOR DETERMINING VOLUME OF A VESSEL

CROSS REFERENCE TO RELATED APPLICATIONS

This application is a National Stage of International Application No. PCT/IE2008/000125 filed Dec. 22, 2008 claiming priority based on S2007/0921 and S2008/0266 filed Dec. 10, 2007 and Apr. 9, 2008, the contents of all of which are incorporated herein by reference in their entirety.

FIELD OF THE INVENTION

The present invention relates to a method and apparatus for determining volume of a vessel, and in particular, though not limited to a method and apparatus for determining volume of a compliant vessel, such as, for example, a biological organ, for example, an oesophagus, a stomach, a pouch in a stomach created during bariatric surgery, or any other such vessel.

BACKGROUND TO THE INVENTION

Apparatus for determining the volume of a vessel is known. Such apparatus typically comprises a catheter extending from a proximal end to a distal end and having a plurality of longitudinally spaced apart electrodes located towards the distal end of the catheter. Two of the electrodes, namely, the two extreme electrodes, typically are stimulating electrodes for receiving a stimulus signal, while the remaining electrodes which are located between the stimulating electrodes are sensing electrodes on which a voltage develops in response to the stimulus signal when the catheter is located in a vessel containing an electrically conductive medium. By providing the stimulus signal as a constant current signal of known current value, and by determining the voltages developed on the sensing electrodes, a determination of the volume of the vessel can be made.

Where it is not feasible to provide an electrically conductive medium in the vessel, the volume of which is to be determined, a balloon catheter is provided whereby a balloon is located on the end of the catheter with the catheter extending through the balloon. The stimulating and sensing electrodes are located on the catheter within the balloon. The balloon is inserted into the vessel the volume of which is to be determined and inflated with an electrically conductive inflating medium. The balloon typically is inflated to fill the vessel, so that the balloon when inflated defines the interior of the vessel. With the balloon defining the interior of the vessel, a stimulus signal is applied to the stimulating electrodes, and resulting voltages on the sensing electrodes are simultaneously read. The volume of the inflated balloon and in turn the volume of the vessel is computed from the read values of the voltages on the sensing electrodes, the value of the current applied to the stimulating electrodes and the electrical resistance of the inflating medium.

However, a problem with such apparatus known heretofore is that it is not possible to determine the volume of a part of the vessel, and additionally, in the case of apparatus which comprise a balloon catheter, it is difficult and in many cases impossible to determine when the balloon has been inflated to a state where it defines the interior of the vessel, since inflating of the balloon may also cause the vessel, the volume of which is to be determined to expand.

There is therefore a need for a method and apparatus for determining volume of a vessel which addresses these problems.

The invention is directed towards a method and apparatus for determining volume of a vessel, and the invention is also directed towards a method and apparatus for determining volume of a part of a vessel, for example, a pouch formed in a stomach during bariatric surgery.

SUMMARY OF THE INVENTION

According to the invention there is provided apparatus for determining volume of a vessel, the apparatus comprising an elongated catheter extending between a proximal end and a distal end, an inflatable expandable element located on the catheter adjacent the distal end thereof with the catheter extending through the expandable element, so that on inflating of the expandable element, the expandable element defines with the catheter an annular hollow interior region, the expandable element being adapted to define the interior of the vessel on inflating of the expandable element in the vessel, at least one stimulating electrode located on one of the catheter and the expandable element within the expandable element, a plurality of longitudinally spaced apart sensing electrodes located on one of the catheter and the expandable element within the expandable element longitudinally spaced apart from the at least one stimulating electrode, a communicating means communicating with the hollow interior region of the expandable element for accommodating an electrically conductive inflating medium, a signal generating means for applying an electrical stimulus signal to the at least one stimulating electrode, and a signal processing means for reading respective signals from at least some of the sensing electrodes in response to the stimulus signal and for computing the volume of the inflated expandable element between at least two axially spaced apart locations from the signals read from the sensing electrodes.

Preferably, the locations between which the volume of the expandable element is computable are selectable.

In one embodiment of the invention an input means is provided for facilitating inputting of a signal for selecting the locations between which the volume of the expandable element is to be computed.

Preferably, the locations between which the volume of the expandable element is computable are locations which correspond to locations in the vessel of reduced transverse cross-section. Advantageously, the signal processing means is adapted for producing a signal indicative of a location at which the vessel is of reduced transverse cross-section.

Preferably, the signal processing means is adapted for outputting a signal indicative of the location of at least one of the sensing electrodes adjacent the location at which the vessel is of reduced transverse cross-section.

Advantageously, the signal processing means is adapted for computing the transverse cross-sectional area of the expandable element adjacent at least one of the locations of the vessel of reduced transverse cross-section.

In one embodiment of the invention the signal processing means is adapted for computing the transverse cross-sectional area of the expandable element adjacent locations corresponding to at least some of the sensing electrodes.

Preferably, the signal processing means is adapted for producing a signal indicative of the approximate external longitudinal profile of the expandable element. Advantageously, the signal processing means is adapted for determining the slope of the approximate external longitudinal profile of the expandable element.

Ideally, the signal processing means is adapted for outputting a signal indicative of a graphical representation of the approximate external longitudinal profile of the expandable element.

In one embodiment of the invention the signal processing means is adapted for determining the locations of the vessel of reduced transverse cross-section as a function of the slope of the longitudinal profile of the expandable element.

In another embodiment of the invention the signal processing means is adapted for computing the transverse cross-sectional area of the inflated expandable element at a location intermediate an adjacent pair of the sensing electrodes with reference to the slope of the approximate external longitudinal profile of the expandable element intermediate the said adjacent pair of the sensing electrodes.

In a further embodiment of the invention the signal processing means is adapted for computing the transverse cross-sectional area of the expandable element at a location intermediate an adjacent pair of the sensing electrodes with reference to the slope of the approximate external longitudinal profile of the expandable element adjacent the said location.

In another embodiment of the invention a visual display screen responsive to signals produced by the signal processing means is provided for displaying the approximate external longitudinal profile of the expandable element graphically.

Preferably, the visual display screen is responsive to signals produced by the signal processing means for displaying a graphical representation of at least some of the sensing electrodes superimposed on the graphical representation of the approximate external longitudinal profile of the expandable element displayed thereon.

Advantageously, the visual display screen is responsive to a signal produced by the signal processing means for displaying the computed volume of the inflated expandable element.

Ideally, the visual display screen is responsive to signals produced by the signal processing means for displaying the computed transverse cross-sectional area of the inflated expandable element at least one location of the inflated expandable element.

In another embodiment of the invention the visual display screen is responsive to signals produced by the signal processing means for displaying the computed transverse cross-sectional area of the inflated expandable element at locations corresponding to each of the sensing electrodes.

In a further embodiment of the invention the visual display screen is responsive to signals produced by the signal processing means for displaying the computed transverse cross-sectional area of the inflated expandable element at locations of reduced transverse cross-sectional area of the inflated expandable element.

In a still further embodiment of the invention a means is provided for determining when the expandable element defines the interior of the vessel.

Preferably, the means for determining when the expandable element defines the interior region of the vessel comprises a pressure sensing means for monitoring the pressure of the inflating medium in the expandable element.

Advantageously, the signal processing means is responsive to a signal from the pressure sensing means indicative of an increase in the pressure of the inflating medium in the expandable element as the inflating medium is being delivered into the expandable element for determining when the expandable element defines the interior of the vessel.

In another embodiment of the invention the signal processing means is responsive to a signal from the pressure sensing means indicative of an increase in the rate of change of pressure of the inflating medium in the expandable element per unit of inflating medium delivered thereto for determining when the expandable element defines the interior of the vessel.

In a further embodiment of the invention the expandable element is adapted so that pressure exerted by the expandable element on the vessel adjacent one of the locations of reduced transverse cross-section of the vessel during expanding of the expandable element is insufficient to dilate the vessel adjacent the location of reduced transverse cross-section.

Preferably, the expandable element is shaped in order to avoid dilation of the vessel adjacent the one of the locations of reduced transverse cross-section thereof during expansion of the expandable element.

Advantageously, a portion of the expandable element is of reduced transverse cross-section for aligning with the location of the vessel of reduced transverse cross-section.

Preferably, the portion of reduced transverse cross-section of the expandable element is located towards one of the distal end and the proximal end thereof.

Advantageously, the portion of reduced transverse cross-section of the expandable element is located adjacent one of the distal end and the proximal end thereof.

In a further embodiment of the invention the expandable element comprises a flexible material. Preferably, the expandable element comprises a resilient material. Ideally, the expandable element is sealably secured to the catheter.

In another embodiment of the invention the communicating means comprises a first lumen extending through the catheter from the proximal end thereof to a location in the catheter within the hollow interior region of the expandable element for accommodating the inflating medium into the expandable element.

In another embodiment of the invention at least one first radial bore extends from the first lumen through the catheter for communicating the first lumen with the hollow interior region of the expandable element.

Preferably, electrically conductive means are provided for electrically coupling the signal generating means with the at least one stimulating electrode and for electrically coupling the signal processing means with the respective sensing electrodes.

In another embodiment of the invention a second lumen extends through the catheter from the proximal end thereof to a location adjacent the stimulating and sensing electrodes for accommodating the electrically conductive means from the signal generating means and the signal processing means to the stimulating and sensing electrodes.

In a further embodiment of the invention the electrically conductive means comprises a plurality of electrically conductive wires, one electrically conductive wire being provided for each one of the stimulating and sensing electrodes.

Preferably, a plurality of second radial bores extend from the second lumen through the catheter within the expandable element for accommodating the electrically conductive wires from the second lumen to the respective stimulating and sensing electrodes.

In another embodiment of the invention a pair of longitudinally spaced apart stimulating electrodes are provided.

Preferably, the sensing electrodes are located between the pair of stimulating electrodes.

In another embodiment of the invention the expandable element comprises a balloon.

In a further embodiment of the invention the apparatus is adapted for determining the volume of a stomach. Preferably, the apparatus is adapted for determining the volume of a part of a stomach.

Advantageously, the apparatus is adapted for determining the volume of a pouch formed in a stomach during or after bariatric surgery.

Ideally, the apparatus is adapted for determining the volume of the pouch between respective locations of the pouch of reduced transverse cross-section.

The invention also provides a method for determining the volume of a vessel, the method comprising providing an elongated catheter which extends between a proximal end and a distal end and having an inflatable expandable element located adjacent the distal end thereof with the catheter extending through the expandable element so that on inflating of the expandable element, the expandable element defines with the catheter an annular hollow interior region, the expandable element being adapted to define the interior of the vessel on inflating of the expandable element in the vessel, providing at least one stimulating electrode on one of the catheter and the expandable element within the expandable element and providing a plurality of longitudinally spaced apart sensing electrodes on one of the catheter and the expandable element within the expandable element longitudinally spaced apart from the stimulating electrode, the method further comprising inserting the distal end of the catheter and the expandable element into the vessel with the expandable element located therein, inflating the expandable element with an electrically conductive inflating medium until the inflated expandable element defines the interior of at least the portion of the vessel the volume of which is to be determined, applying an electrical stimulus signal to the at least one stimulating electrode, and reading signals from at least some of the respective sensing electrodes in response to the stimulus signal, computing the volume of the inflated expandable element between at least two axially spaced apart locations from the signals read from the sensing electrodes.

Preferably, the locations between which the volume of the inflated expandable element is computable are selectable.

In one embodiment of the invention an input means is provided for facilitating inputting of a signal for selecting the locations between which the volume of the inflated expandable element is to be computed.

In another embodiment of the invention the locations between which the volume of the inflated expandable element is computable are locations which correspond to locations in the vessel of reduced transverse cross-section.

Preferably, the locations in the vessel of reduced transverse cross-section are identified from signals read from the sensing electrodes in response to the stimulus signal.

In another embodiment of the invention a signal indicative of a location at which the vessel is of reduced transverse cross-section is produced. Preferably, a signal is produced indicative of the location of at least one of the sensing electrodes adjacent the location at which the vessel is of reduced transverse cross-section. Advantageously, the signals from the sensing electrodes are processed for producing a signal indicative of the identity of the sensing electrode at the locations at which the inflated expandable element is of reduced transverse cross-section.

In one embodiment of the invention the identified sensing electrodes adjacent the locations at which the inflated expandable element is of reduced transverse cross-section are selected as the sensing electrodes between which the volume of the vessel is to be computed.

In another embodiment of the invention the volume of the inflated expandable element between the locations of the identified ones of the sensing electrodes adjacent the locations at which the inflated expandable element is of reduced transverse cross-section is computed, and a signal indicative of the volume of the expandable element between the said locations is produced.

In a further embodiment of the invention an approximate external longitudinal profile of the expandable element is computed from the signals read from the sensing electrodes in response to the stimulus signal applied to the at least one stimulating electrode. Preferably, a signal indicative of the approximate external longitudinal profile of the expandable element is produced.

Preferably, a graphical representation of the approximate external longitudinal profile of the expandable element is displayed. Advantageously, the locations between which the volume of the inflated expandable element is to be computed are selected from the displayed graphical representation of the approximate external longitudinal profile of the inflated expandable element. Preferably, a graphical representation of at least some of the sensing electrodes is displayed superimposed on the displayed graphical representation of the approximate external longitudinal profile of the inflated expandable element.

In another embodiment of the invention the ones of the sensing electrodes, the graphical representation of which is displayed are displayed with respective corresponding identities for facilitating selection of the locations between which the volume of the inflated expandable element is to be computed.

In another embodiment of the invention the sensing electrodes are represented in the graphical representation thereof by respective lines extending transversely relative to the displayed approximate external longitudinal profile of the inflated expandable element.

In another embodiment of the invention the slope of the approximate external longitudinal profile of the inflated expandable element is computed for determining the locations along the inflated expandable element of reduced transverse cross-section.

In a further embodiment of the invention the transverse cross-sectional area of the inflated expandable element at a location intermediate an adjacent pair of the sensing electrodes is computed with reference to the slope of the approximate external longitudinal profile of the expandable element intermediate the said adjacent pair of sensing electrodes. Preferably, the transverse cross-sectional area of the inflated expandable element at a location intermediate an adjacent pair of the sensing electrodes is computed with reference to the slope of the approximate external longitudinal profile of the expandable element at the said location.

In one embodiment of the invention the locations of the vessel of reduced transverse cross-section are determined as a function of the slope of the approximate external longitudinal profile of the inflated expandable element.

Preferably, the transverse cross-sectional area of the inflated expandable element at the locations thereof of reduced transverse cross-section is computed from signals read from the sensing electrodes in response to the stimulus signal applied to the at least one stimulating electrode.

Advantageously, the computed values of the transverse cross-sectional areas of the inflated expandable element adjacent the locations of reduced transverse cross-sectional area are displayed.

Preferably, the transverse cross-sectional area of the inflated expandable element at spaced apart locations corresponding to at least some of the sensing electrodes is computed.

Advantageously, the computed values of the transverse cross-sectional areas of the inflated expandable element at locations adjacent the at least some of the sensing electrodes are displayed.

In one embodiment of the invention the transverse cross-sectional area of the inflated expandable element at a location intermediate a pair of adjacent ones of the sensing electrodes is computed by interpolating between the computed transverse cross-sectional areas of the inflated expandable element adjacent the respective ones of the pair of adjacent ones of the sensing electrodes.

Preferably, the volume of the inflated expandable element between the spaced apart locations is computed as a function of the computed transverse cross-sectional areas of the inflated expandable element.

Advantageously, the volume of the inflated expandable element between the spaced apart locations is computed as a function of the spacings between adjacent pairs of the respective sensing electrodes adjacent the locations at which the transverse cross-sectional area of the inflated expandable element is computed and which are located between the locations between which the volume of the inflated expandable element is to be computed.

Ideally, the computed value of volume of the inflated expandable element between the spaced apart locations is displayed.

In another embodiment of the invention the pressure of the inflating medium is monitored during expansion of the expandable element to determine when the expandable element defines at least the portion of the interior of the vessel the volume of which is to be determined. Advantageously, the expandable element is determined as defining at least the portion of the interior of the vessel the volume of which is to be determined when the pressure of the inflating medium in the hollow interior region of the expandable element increases during delivery thereof into the hollow interior region of the expandable element.

Preferably, the expandable element is determined as defining at least the portion of the interior of the vessel the volume of which is to be determined when the rate of change of pressure of the inflating medium in the expandable element per unit of inflating medium delivered into the hollow interior region of the expandable element increases.

In one embodiment of the invention a pair of stimulating electrodes are provided spaced apart longitudinally along the catheter. Preferably, the sensing electrodes are located between the pair of stimulating electrodes.

Preferably, a visual display screen is provided.

In one embodiment of the invention the method is adapted for determining the volume of a stomach. Preferably, the method is adapted for determining the volume of a part of a stomach. Advantageously, the method is adapted for determining the volume of a pouch formed in a stomach during bariatric surgery. Ideally, the method is adapted for determining the volume of the pouch between respective locations of the pouch of reduced transverse cross-section.

The invention also provides a method for determining the volume of a pouch formed in a stomach by bariatric surgery, the method comprising providing an elongated catheter which extends between a proximal end and a distal end and which comprises an inflatable expandable element located adjacent the distal end thereof with the catheter extending through the expandable element so that on inflating of the expandable element the expandable element defines with the catheter an annular hollow interior region, the expandable element being adapted to define the interior of a part of the stomach comprising the pouch on inflating of the expandable element therein, providing at least one stimulating electrode on one of the catheter and the expandable element within the expandable element, and providing a plurality of longitudinally spaced apart sensing electrodes on one of the catheter and the expandable element within the expandable element longitudinally spaced apart from the at least one stimulating electrode, the method further comprising inserting the distal end of the catheter and the expandable element into the part of the stomach including the pouch, expanding the expandable element with an electrically conductive inflating medium until the expandable element defines the interior of the part of the stomach including the pouch, applying an electrical stimulus signal to the at least one stimulating electrode, and reading signals from at least some of the sensing electrodes in response to the stimulus signal, computing the volume of the inflated expandable element between at least two axially spaced apart locations corresponding to the oesophageal sphincter and the stoma from the signals read from the sensing electrodes.

In one embodiment of the invention the two spaced apart locations between which the volume of the inflated expandable element is computable are selected.

In another embodiment of the invention an approximate external longitudinal profile of the inflated expandable element is computed from the signals read from at least some of the sensing electrodes in response to the stimulus signal applied to the at least one stimulating electrode. Preferably, a signal indicative of the approximate external longitudinal profile of the expandable element is produced. Advantageously, a graphical representation of the approximate external longitudinal profile of the inflated expandable element is displayed.

Preferably, the locations between which the volume of the inflated expandable element is to be computed are selected from the displayed graphical representation of the approximate external longitudinal profile of the inflated expandable element.

Advantageously, a graphical representation of at least some of the sensing electrodes is displayed superimposed on the displayed graphical representation of the approximate external longitudinal profile of the inflated expandable element.

In one embodiment of the invention the ones of the sensing electrodes, the graphical representation of which is displayed are displayed with respective corresponding identities for facilitating selection of the locations between which the volume of the inflated expandable element is to be computed.

Preferably, the sensing electrodes are represented in the graphical representation thereof by respective lines extending transversely relative to the displayed approximate external longitudinal profile of the inflated expandable element.

Advantageously, the locations between which the volume of the inflated expandable element is to be computed are selected by selecting the two electrodes of the sensing electrodes adjacent the respective locations.

In one embodiment of the invention the locations between which the volume of the inflated expandable element is to be computed are locations which correspond to locations at which the inflated expandable element is of reduced transverse cross-section. Preferably, the locations of reduced transverse cross-section are identified from signals read from at least some of the sensing electrodes in response to a stimulus signal being applied to the at least one stimulating electrode.

Advantageously, a signal indicative of each location of reduced transverse cross-section is produced.

Preferably, the signal indicative of each location of reduced transverse cross-section is indicative of the identity of the one of the sensing electrodes adjacent the location of reduced transverse cross-section.

In another embodiment of the invention the signals from at least some of the sensing electrodes are processed for producing the signals indicative of the identity of the ones of the sensing electrodes adjacent the locations at which the inflated expandable element is of reduced transverse cross-section.

In a further embodiment of the invention the identities of the ones of the sensing electrodes adjacent the locations at which the inflated expandable element is of reduced transverse cross-section are selected as the electrodes between which the volume corresponds to the volume of the pouch.

In another embodiment of the invention the slope of the approximate external longitudinal profile of the inflated expandable element is computed for determining the locations along the inflated expandable element of reduced transverse cross-section. Preferably, the locations of reduced transverse cross-section are determined as a function of the slope of the approximate external longitudinal profile of the inflated expandable element.

In one embodiment of the invention the transverse cross-sectional area of the inflated expandable element at a location intermediate an adjacent pair of the sensing electrodes is computed with reference to the slope of the approximate external longitudinal profile of the expandable element intermediate the said adjacent pair of sensing electrodes.

In another embodiment of the invention the transverse cross-sectional area of the inflated expandable element at a location intermediate an adjacent pair of the sensing electrodes is computed with reference to the slope of the approximate external longitudinal profile of the expandable element at the said location.

Preferably, the transverse cross-sectional area of the inflated expandable element at the locations thereof of reduced transverse cross-section is computed from signals read from the sensing electrodes in response to the stimulus signal applied to the at least one stimulating electrode.

Advantageously, the computed values of the transverse cross-sectional areas of the inflated expandable element adjacent the locations of reduced transverse cross-sectional area are displayed. Preferably, the transverse cross-sectional area of the inflated expandable element at spaced apart locations corresponding to at least some of the sensing electrodes is computed.

In one embodiment of the invention the computed values of the transverse cross-sectional area of the inflated expandable element at the spaced apart locations corresponding to at least some of the sensing electrodes is displayed.

In another embodiment of the invention the transverse cross-sectional area of the inflated expandable element at a location intermediate a pair of adjacent ones of the sensing electrodes is computed by interpolating between the computed transverse cross-sectional areas adjacent the said adjacent ones of the sensing electrodes.

Preferably, the volume of the inflated expandable element between the spaced apart locations is computed as a function of at least some of the computed transverse cross-sectional areas of the inflated expandable element.

Advantageously, the volume of the inflated expandable element between the spaced apart locations is computed as a function of the spacings between adjacent pairs of the respective sensing electrodes adjacent the locations at which the transverse cross-sectional area of the inflated expandable element is computed and which are located between the locations between which the volume of the inflated expandable element is to be computed.

Preferably, the computed value of volume of the inflated expandable element between the spaced apart locations is displayed.

In another embodiment of the invention the pressure of the inflating medium is monitored during inflating of the expandable element to determine when the expandable element defines the interior of the pouch. Preferably, the expandable element is determined as defining the interior of the pouch in response to an increase in the pressure of the inflating medium in the expandable element during delivery thereof into the hollow interior region of the expandable element.

Advantageously, the expandable element is determined as defining the interior of the pouch in response to an increase in the rate of change of pressure of the inflating medium in the expandable element per unit of inflating medium delivered into the hollow interior region of the expandable element during inflating thereof.

In one embodiment of the invention an input means is provided for facilitating inputting of a signal for selecting the locations between which the volume of the inflated expandable element is to be computed.

Preferably, a visual display unit is provided.

The invention also provides a balloon catheter comprising an elongated catheter extending between a proximal end and a distal end, an inflatable expandable element located on the catheter adjacent the distal end thereof with the catheter extending through the expandable element, so that on inflation of the expandable element, the expandable element defines with the catheter an annular hollow interior region, the expandable element being adapted to define the interior of the vessel on inflating of the expandable element in the vessel, at least one stimulating electrode located on one of the catheter and the expandable element within the expandable element, a plurality of longitudinally spaced apart sensing electrodes located on one of the catheter and the expandable element within the expandable element longitudinally spaced apart from the at least one stimulating electrode, wherein a portion of the expandable element adjacent one of a proximal end and a distal end of the expandable element is shaped in order to minimise dilation of the vessel adjacent a location thereof of reduced transverse cross-section during expansion of the expandable element.

In one embodiment of the invention the expandable element is of reduced transverse cross-section adjacent the one of the proximal end and the distal end of the expandable element.

ADVANTAGES OF THE INVENTION

The advantages of the invention are many. A particularly important advantage of the invention is that it provides an apparatus and a method for determining the volume of a part of a vessel, as well as for determining the entire volume of a vessel. A further advantage of the invention is that it allows the volume of the vessel or a part thereof to be determined without the risk of expansion of the vessel the volume of which is to be determined.

BRIEF DESCRIPTION OF THE DRAWINGS

The invention will be more clearly understood from the following description of some preferred embodiments thereof, which are given by way of example only, with reference to the accompanying drawings, in which.

DETAILED DESCRIPTION OF THE INVENTION

Referring to the drawings and initially to FIGS. 1 to 4 thereof, there is illustrated apparatus according to the invention, indicated generally by the reference numeral 1, for determining volume of a vessel. In this embodiment of the invention the apparatus 1 is particularly suitable for determining volume of a pouch 2 created in the stomach 3 of a subject by bariatric surgery, whereby a lap-band 18 is located around the exterior of the stomach 3 to form the pouch 2, see FIG. 4. Accordingly, the apparatus 1 is particularly suitable for determining volume of a selectable part of a vessel. The apparatus 1 comprises a balloon catheter 5 having an elongated catheter 6 extending between a proximal end 7 and a distal end 8. An expandable element, which in this case comprises an inflatable balloon 10 is located on and sealably secured to the catheter 6 adjacent the distal end 8 with the catheter 6 extending through the balloon 10, so that the balloon 10 when inflated defines with the catheter 6 an annular hollow interior region 12.

The balloon 10 is adapted for locating in the pouch 2 of the stomach 3, so that when inflated the balloon 10 defines the interior of the pouch 2 and a lower portion of the oesophagus 11 as well as the lower oesophageal sphincter 13 and a stoma 4 formed between the pouch 2 and an upper portion 9 of the stomach 3 during the bariatric surgery. Therefore by determining the volume of the portion of the inflated balloon 10 in the pouch 2, the volume of the pouch 2 is determined, as will be described below. The balloon 10 is of a flexible elastic material with a relatively high coefficient of elastic expansion, so that the pressure required to expand the balloon 10 to define the pouch 2 is relatively low.

A pair of stimulating electrodes 14 are located on the catheter 6 within the hollow interior region 12 of the balloon 10 and are longitudinally spaced apart along the catheter 6. A plurality of sensing electrodes 15 are also located on the catheter 6 within the hollow interior region 12 of the balloon 10 between the stimulating electrodes 14, and are longitudinally spaced apart from each other along the catheter 6 and are also longitudinally spaced apart from the stimulating electrodes 14. In this embodiment of the invention the sensing electrodes 15 are equi-spaced apart longitudinally from each other, and the stimulating electrodes 14 are each equi-spaced apart from the corresponding adjacent sensing electrode 15. The spacing between the stimulating electrodes 14 and their respective corresponding adjacent sensing electrodes 15 is similar to the spacing between adjacent ones of the sensing electrodes 15. However, the spacing between the stimulating electrodes 14 and the adjacent ones of the sensing electrodes 15 may be different to the spacing between the sensing electrodes 15, and in many cases the spacing between the stimulating electrodes 14 and the adjacent ones of the sensing electrodes 15 may be greater than the spacing between the sensing electrodes 15. Indeed, in certain cases the spacing between the sensing electrodes may vary, but would be known. The stimulating and sensing electrodes 14 and 15 are band type electrodes of electrically conductive metal foil and extend completely around the catheter 6.

Figure 2:
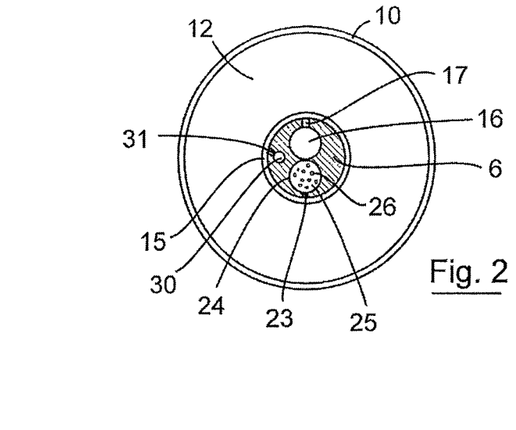
FIG. 2 is a transverse cross-sectional end elevational view of a portion of the apparatus of FIG. 1 on the line II-II of FIG. 1.

A communicating means comprising a first lumen 16 extending longitudinally through the catheter 6 from the proximal end 7 to a location within the balloon 10, and a pair of radially extending first bores 17 extending through the catheter 6 from the first lumen 16 to the hollow interior region 12 are provided for accommodating an electrically conductive inflating medium to the hollow interior region 12 of the balloon 10 for inflating thereof, see FIG. 2. A pump 19 delivers the electrically conductive inflating medium, which in this embodiment of the invention is a saline solution from a reservoir 20 through a fluid line 22 which is coupled to the first lumen 16 adjacent the proximal end 7 of the catheter 6.

A second lumen 24 extends longitudinally through the catheter 6 from the proximal end 7 to the stimulating and sensing electrodes 14 and 15 for accommodating a plurality of mutually insulated electrically conductive wires 25 and 26 to the respective stimulating and sensing electrodes 14 and 15, respectively. In this embodiment of the invention two wires 25 are provided, one for each stimulating electrode 14, and the number of wires 26 is similar to the number of sensing electrodes, so that one wire 26 is provided for each sensing electrode 15. Second bores 23 extend radially through the catheter 6 from the second lumen 24 for accommodating the respective wires 25 and 26 from the second lumen 24 to the corresponding stimulating and sensing electrodes 14 and 15. The wires 25 are coupled to a signal generator 27, which generates and applies an electrical stimulus signal, namely, an electrical constant current signal of known current value to the stimulating electrodes 14. The wires 26 are coupled to a signal processing means, namely, a microprocessor 28, which reads signals, namely, voltage signals on the sensing electrodes 15 in response to the stimulus current signal applied to the stimulating electrodes 14 which is conducted through the saline solution in the hollow interior region 12 when the balloon 10 is inflated to the sensing electrodes 15. The microprocessor 28 is operable to compute the volume of the inflated balloon 10 from the voltage signals read from the sensing electrodes 15, for in turn determining the volume of the pouch 2 by determining the volume of the portion of the balloon 10 in the pouch 2, as will be described below. The signal generator 27 is operable under the control of the microprocessor 28 for applying the stimulus signal to the stimulating electrodes 14.

A third lumen 30 extends longitudinally through the catheter 6 from the proximal end 7 to a location within the balloon 10, and a third radial bore 31 extending through the catheter 6 within the balloon 10 communicates the third lumen 30 with the hollow interior region 12 of the balloon 10. A pressure sensing means, namely, a pressure sensor 33 communicates with the hollow interior region 12 of the balloon 10 through the third lumen 10 and the third radial bore 31, and through a pipeline 34 for monitoring the pressure of the saline solution in the balloon 10 during inflating thereof, so that a determination as to when the balloon 10 defines the interior of the pouch 2 can be made.

In this embodiment of the invention the pressure sensor 33 provides a visual readout of the pressure of the saline solution in the balloon 10, and can be physically read by an individual operating the pump 19 to inflate the balloon 10 with the saline solution. In this embodiment of the invention the pump 19 pumps the saline solution at a constant rate. Therefore, the balloon 10 is determined as defining the interior of the pouch 2 when the rate of change of pressure of the saline solution in the balloon 10 per unit of inflating medium delivered to the balloon 10 commences to increase significantly during inflating of the balloon 10. Since the balloon 10 is of a flexible material with a relatively high coefficient of elastic expansion, the pressure required to expand the balloon 10 up to a state where it fills the pouch 2, in other words, defines the interior of the pouch 2 is relatively low, and also increases at a relatively low rate. In other words, the rate of change of the pressure in the balloon per unit volume of saline solution delivered to the balloon 10 is relatively low and is substantially constant until the balloon 10 defines the interior of the pouch 2. However, once the balloon has been expanded to define the interior of the pouch 2, further delivery of saline solution into the balloon 10 causes the balloon 10 to act on the wall of the pouch 2 to in turn attempt to expand the pouch 2. Since the wall of the pouch 2 is considerably less elastic than the balloon 10, when the balloon 10 defines the interior of the pouch 2, the rate of change of pressure in the saline solution per unit volume of saline solution delivered to the balloon 10 suddenly increases significantly, thus indicating that the balloon 10 has been inflated to a state where the balloon 10 defines the interior of the pouch 2. At this stage, the pressure of the saline solution in the balloon 2 is slightly reduced to the pressure of the saline solution just prior to the increase in the rate of change of pressure in the saline solution, in order to avoid any danger of the pouch 2 being expanded by the balloon 10. Thus, the balloon 10 is determined as defining the interior of the pouch 2 at the pressure displayed by the pressure sensor 33 just prior to the sudden jump in the rate of change of pressure of the saline solution in the balloon 10.

It is envisaged that a flow meter (not shown) may be located in the fluid line for monitoring the volume rate of delivery of the saline solution into the balloon 10, and electrical output signals indicative of the volume rate of delivery of saline solution into the balloon 10 from the flow meter would be fed to the microprocessor 28. Additionally, electrical output signals from the pressure sensor 33 indicative of the pressure of the saline solution in the balloon 10 would also be fed to the microprocessor 28. The microprocessor 28 would then read the signals from the flow meter and the pressure sensor 33 for determining when a jump in the rate of change of pressure of the saline solution per unit of volume of the saline solution delivered to the balloon 10 occurs during inflating thereof. The pump 19 could be operated under the control of the microprocessor 28, and on the microprocessor 28 determining that the inflated balloon defined the interior of the pouch 2, the pump 19 would be deactivated.

Returning now to the microprocessor 28, the microprocessor 28 is programmed to control the signal generator 27 for outputting the stimulus signal which is of known constant current value to the stimulating electrodes 14, and for simultaneously reading the respective voltage signals on the sensing electrodes 15 in response to the stimulus current signal when the balloon 10 is inflated with the saline solution to define the interior of the pouch 2. By determining the voltage on the respective sensing electrodes 15, the electrical impedance of the saline solution between the stimulating electrodes 14 and the two adjacent sensing electrodes 15, and also between adjacent pairs of the sensing electrodes 15 can be determined.

The electrical impedance of the saline solution between each adjacent pair of the sensing electrodes 15 is inversely proportional to the transverse cross-sectional area of the inflated balloon 10 adjacent the relevant pair of the sensing electrodes 15, and is proportional to the distance between the relevant pair of sensing electrodes 15. Since the distance between adjacent pairs of the sensing electrodes 15 is similar, the electrical impedance between adjacent pairs of the sensing electrodes 15 can be taken as being equal to a constant times the inverse of the transverse cross-sectional area of the balloon 10 adjacent the corresponding pair of sensing electrodes 15. The voltage drop between adjacent pairs of the sensing electrodes 15 is equal to the product of the impedance of the saline solution between the corresponding adjacent pairs of sensing electrodes 15 and the known value of the constant stimulus current. Therefore, the transverse cross-sectional area of the balloon adjacent each adjacent pair of sensing electrodes 15 is inversely proportional to the voltage drop between the corresponding adjacent pair of the sensing electrodes 15, and is therefore equal to a constant times the inverse of the product of the voltage drop by the known value of the constant stimulus current. The microprocessor 28 is programmed to compute the transverse cross-sectional area of the balloon adjacent the respective sensing electrodes 15 from the following equation:

$$A = \frac{K}{VI}$$

where
- A is the transverse cross-sectional area of the balloon adjacent one of the sensing electrodes,
- I is the value of the current of the stimulus signal applied to the stimulating electrodes 14,
- V is the voltage drop between the sensing electrodes and the next adjacent sensing electrode, and
- K is a constant determined from the impedance per unit volume of the saline solution and the spacing between adjacent pairs of the sensing electrodes.

Since the spacing between the sensing electrodes 15 is known, and is constant, by determining the transverse cross-sectional area of the balloon 10 adjacent one of the sensing electrodes 15, the volume of the balloon 10 between that sensing electrode 15 and the next adjacent sensing electrode 15 can be determined by multiplying the transverse cross-sectional area of the balloon 10 adjacent the sensing electrode 15 by the spacing between that sensing electrode 15 and the next adjacent sensing electrode 15, assuming that the spacing between the sensing electrodes 15 is sufficiently small that any variation in the transverse cross-sectional area of the inflated balloon 10 between adjacent pairs of the sensing electrodes 15 will be relatively small. Accordingly, by computing the volume of the balloon between adjacent pairs of the sensing electrodes 15, the total volume of the balloon 10 between any two selected sensing electrodes 15 can be readily determined by merely summing the volumes between the respective pairs of the sensing electrodes 15 which are located between the two selected sensing electrodes 15 between which the volume of the balloon 10 is to be determined.

The microprocessor 28 is programmed to compute the transverse cross-sectional area of the inflated balloon 10 adjacent the respective sensing electrodes 15. On computing the respective transverse cross-sectional areas of the inflated balloon 10, the microprocessor 28 is programmed to compute the volume of the inflated balloon 10 between the adjacent pairs of the sensing electrodes 15 by multiplying the transverse cross-sectional area of the inflated balloon 10 at each of the sensing electrodes 15 by the distance between each pair of sensing electrodes 15. The microprocessor 28 is programmed to compute the total volume of the inflated balloon 10 by summing the respective computed volumes of the inflated balloon 10 between the adjacent pairs of the sensing electrodes 15. Additionally, the microprocessor 28 is programmed to compute the volume of the inflated balloon 10 between any two selectable locations corresponding to any two of the sensing electrodes 15. The volume between two selected ones of the sensing electrodes 15 is computed by summing the computed volumes between the adjacent pairs of the sensing electrodes between the two selected ones of the sensing electrodes 15. Thus, by selecting two of the sensing electrodes 15, the volume of a part of the balloon can be readily determined.

Figure 3:
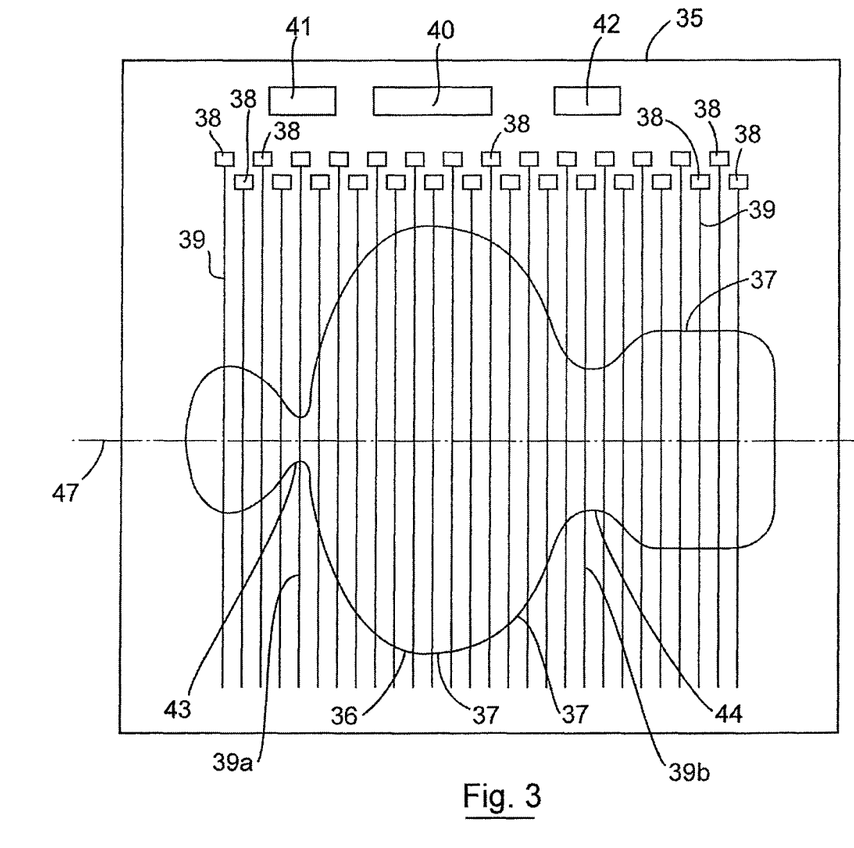
FIG. 3 is a graphical representation of a profile produced by the apparatus of FIG. 1.

The microprocessor 28 from the computed transverse cross-sectional areas of the inflated balloon 10 adjacent the respective sensing electrodes 15 is programmed to compute an approximate external longitudinal profile of the inflated balloon 10 which is based on the respective computed transverse cross-sectional areas, assuming the inflated balloon 10 is symmetrical about its central longitudinal axis, see FIG. 3. In cases where the pouch and in turn the inflated balloon 10 is symmetrical about the central longitudinal axis of the balloon 10, the approximate external longitudinal profile of the balloon 10 computed by the microprocessor 28 is a relatively accurate representation of the actual external longitudinal profile of the balloon 10. However, in cases where the pouch 2, and in turn the inflated balloon 10 is not symmetrical about the central longitudinal axis of the balloon 10, the approximate external longitudinal profile of the balloon 10 computed by the microprocessor 28 will be only a very approximate representation of the actual external longitudinal profile of the balloon 10, and the more asymmetrical the balloon becomes relative to its longitudinal central axis, the less representative the computed approximate external longitudinal profile of the balloon 10 will be of the actual external longitudinal profile of the balloon 10. However, the computed values of transverse cross-sectional area of the balloon 10 at the locations corresponding to the locations of the respective sensing electrodes 15 will be a relatively accurate value of the actual transverse cross-sectional areas, since the transverse cross-sectional areas of the balloon 10 are computed independently of the shape of the balloon 10.

A visual display screen 35 is operated under the control of the microprocessor 28 for displaying a graphical representation 36 of the approximate external longitudinal profile of the inflated balloon 10 computed by the microprocessor 28. The graphical representation 36 of the approximate external longitudinal profile of the inflated balloon 10 is illustrated by the curved lines 37 on the visual display screen 35. The microprocessor 28 also outputs signals to the visual display screen 35 which are indicative of the locations of the respective sensing electrodes 15 relative to the graphical representation 36 of the approximate external longitudinal profile of the inflated balloon 10 for display on the visual display screen 35. The locations of the sensing electrodes 15 relative to the graphical representation 36 of the inflated balloon 10 are represented by the transverse lines 39 on the visual display screen 35.

Windows 38 in the visual display screen 35 display the values of the computed transverse cross-sectional areas of the balloon 10 at the locations corresponding to the locations of the respective sensing electrodes 15. A window 40 in the visual display screen 35 displays the computed value of the volume of the inflated balloon 10 or a selected part of the volume thereof. Windows 41 and 42 display the computed transverse cross-sectional areas of the inflated balloon 10 at the locations which correspond to the locations of the stoma 4 of the pouch 2 and the lower oesophageal sphincter 13, namely, at the locations 43 and 44, respectively, on the graphical representation 36 of the inflated balloon 10.

An input means, namely, a keyboard 45 and a mouse 46 are provided for facilitating inputting of data and commands into the microprocessor 28. A user wishing to select the part of the inflated balloon 10 the volume of which is to be computed selects the relevant two of the transverse lines 39 which represent the relevant two of the sensing electrodes 15 between which the volume of the inflated balloon 10 is to be computed for display in the window 40. The relevant two of the transverse lines 39 are selected by moving a cursor (not shown) displayed on the visual display screen 35 to select the relevant two of the transverse lines 39. This selection may be made through the mouse 46 or the keyboard 45. This permits a user by inspecting the graphical representation 36 of the approximate external longitudinal profile of the balloon 10 displayed on the visual display screen 35 to select the sensing electrodes 15 between which the volume of the balloon 10 is to be determined. For example, by selecting the part of the balloon 10 between the two locations 43 and 44 at which the inflated balloon 10 is of reduced transverse cross-sectional area, which result from pressure on the balloon 10 caused by the stoma 4 and the oesophageal sphincter 13 between which the pouch 2 is formed, the volume of the pouch 2 is computed by the microprocessor 28 and displayed in the window 40 in the display screen 35.

Alternatively, the visual display screen may be a touch screen, and the locations between which the volume of the balloon 10 is to be computed would be selected by touching the screen adjacent the two transverse lines 39 between which the volume of the balloon 10 is to be computed.

The microprocessor 28 is also programmed to determine the locations 43 and 44 on the approximate external longitudinal profile of the inflated balloon 10, which correspond to the stoma 4 and the lower oesophageal sphincter 13. To do this, the microprocessor 28 is programmed to determine the locations of reduced transverse cross-section of the inflated balloon 10. This is carried out by determining the points of inflection along the curved lines 37 which represent the approximate external longitudinal profile of the inflated balloon 10. The points of inflection are determined by computing the slope of the curved lines 37 representing the approximate external longitudinal profile of the balloon 10 with respect to a central axis 47 of the graphical representation 36. The slope of the curved lines 37 is computed by computing the derivatives of the curved lines 37 with respect to the distance along the central axis 47, and the points of inflection along the curved lines 37 are obtained by equating the derivatives to zero. A negative derivative value is indicative of a reducing transverse cross-sectional area, while a positive derivative is indicative of an increasing transverse cross-sectional area. Thus, a derivative value of the curved lines 37 of the approximate external longitudinal profile of the inflated balloon 10 with respect to distance along the catheter 6 of zero value when the derivative value transitions through the zero value from a negative derivative value to a positive derivative value is determined as being indicative of a location of a point of inflection on the lines 37, which correspond to a location of reduced transverse cross-section of the inflated balloon 10.

Where a point of inflection on the curved lines 37 representing the approximate external longitudinal profile of the balloon 10 corresponding to a location of reduced transverse cross-section of the balloon 10 does not coincide with one of the transverse lines 39 on the visual display screen 35, in other words, when the point of inflection is located at a location between an adjacent pair of the sensing electrodes 15, the transverse cross-sectional area of the balloon 10 at the relevant point of inflection is computed based on the computed slope of the curved lines 37 of the approximate external longitudinal profile between the adjacent pair of sensing electrodes 15. Alternatively, the transverse cross-sectional area corresponding to the relevant point of inflection is determined by interpolating between the computed transverse cross-sectional areas of the balloon 10 at the adjacent pair of sensing electrodes 15. The computed transverse cross-sectional area of the balloon 10 at the relevant point of inflection is displayed in the corresponding one of the windows 41 and 42. Additionally, in this case the volume of the balloon 10 between the two locations of reduced transverse cross-section which correspond to the respective points of inflection is computed between the respective points of inflection, even when the points of inflection do not coincide with the locations of any of the sensing electrodes, since the distance of each point of inflection from the adjacent sensing electrode 15 can be computed, and the volume or volumes of the balloon 10 between the relevant point of inflection and the adjacent sensing electrode 15 is also computed. This or these computed values are then added to the summed values of the computed values of the volume of the balloon between the relevant sensing electrodes 15 between the points of inflection. In cases where the visual display screen is a touch screen, the locations between the volume of the balloon 10 is to be computed can be selected as locations between adjacent pairs of sensing electrodes 15, and the volume of the balloon 10 between the selected locations would be similarly computed by computing the volume of the balloon 10 between each selected location and the adjacent sensing electrode 15, and summing these computed values with the sum of the computed values of the volume of the balloon 10 between the respective relevant adjacent sensing electrodes 15.

Figure 1:
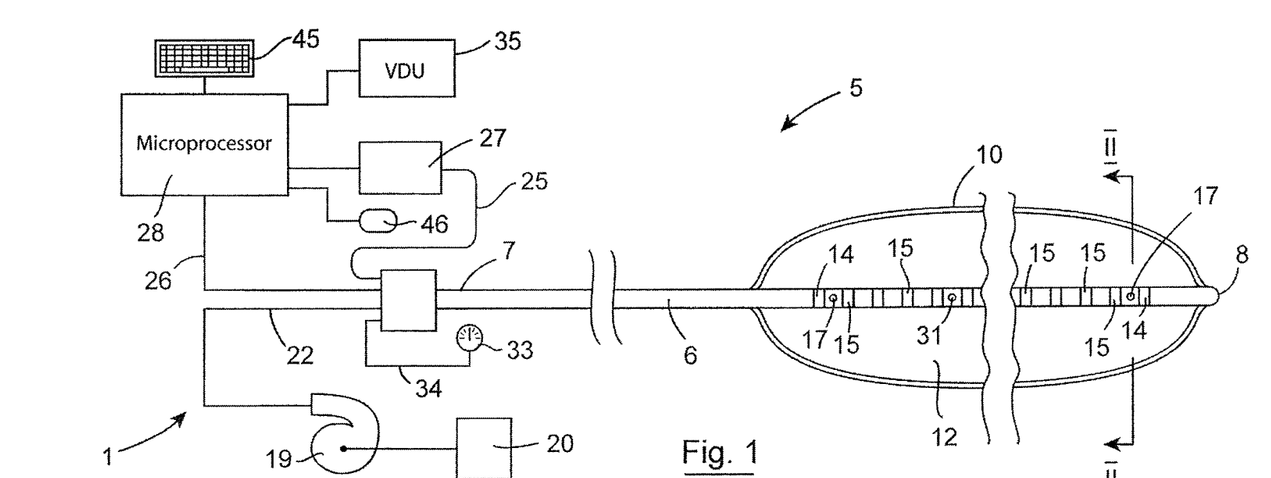
FIG. 1 is a partly schematic side elevational view and partly block representational view of apparatus according to the invention for determining volume of a biological organ.
Figure 4:
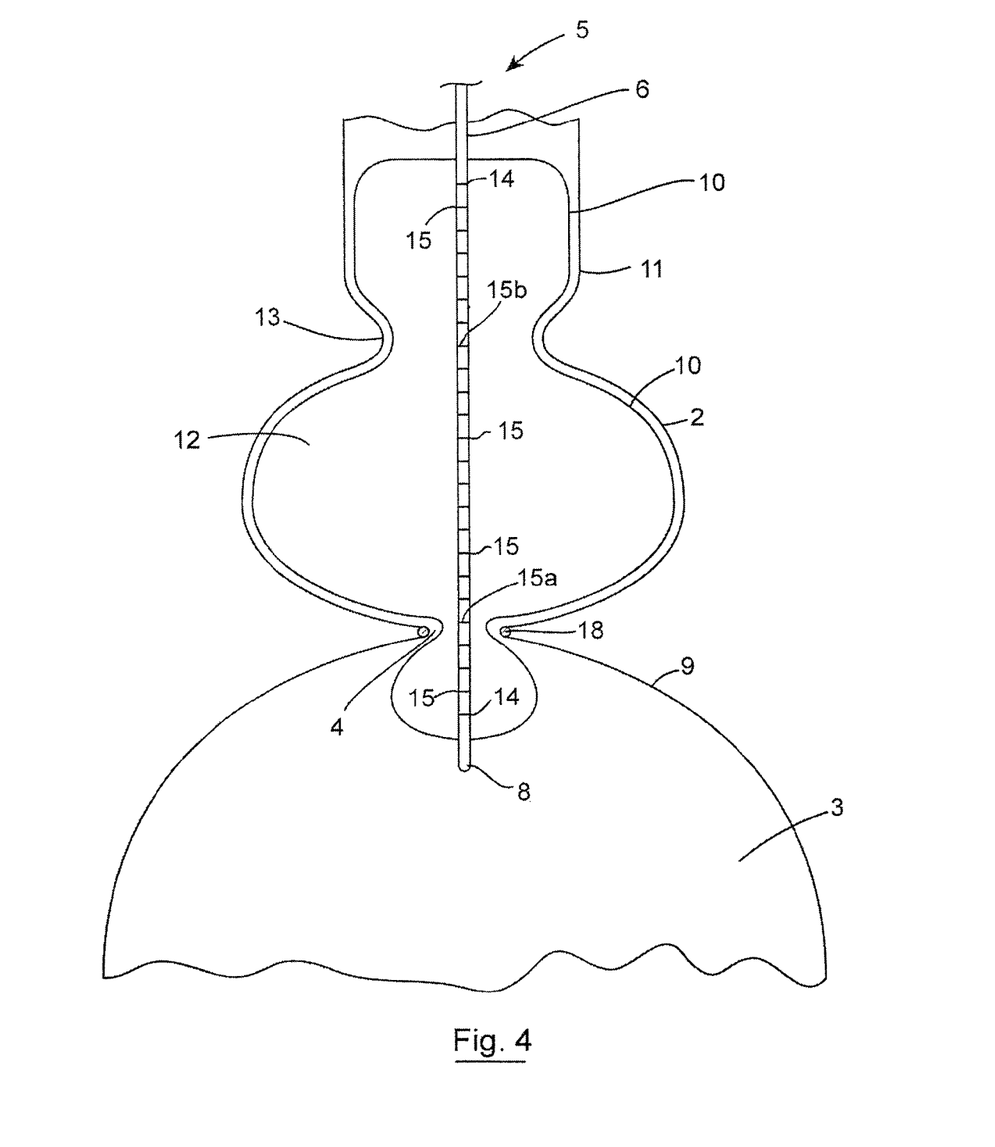
FIG. 4 is a transverse cross-sectional side elevational view of the apparatus of FIG. 1 in use.

Referring now to FIGS. 3 and 4, use of the apparatus 1 of FIGS. 1 and 2 for determining the volume of the pouch 2 created in the stomach 3 of a subject during bariatric surgery, whereby the pouch 2 is formed by the lap-band 18, will now be described. With the balloon 10 deflated, the balloon catheter 5 is inserted by an endoscope or directly either trans-nasally or trans-orally through the oesophagus 11 into the stomach 3 as illustrated in FIG. 4 until the balloon 10 is located in the pouch 2 with the distal end 8 of the catheter 6 and a distal portion of the balloon 10 extending downwardly into the upper portion 9 of the stomach 3. The balloon 10 is then inflated by the pump 19 with the saline solution. During inflating of the balloon 10 the pressure of the saline solution in the balloon 10 is monitored on the pressure sensor 33. On a sudden increase in the rate of change of the pressure of the saline solution per unit volume thereof delivered into the balloon 10 being detected, inflating of the balloon 10 is terminated and the pressure in the saline solution is reduced by bleeding a small volume of the saline solution from the balloon 10 until the pressure in the saline solution is equal to the pressure just prior to the sudden increase in the rate of change of the pressure in the saline solution. At that stage the inflated balloon is determined as being inflated to a state which defines the pouch 2.

The microprocessor 28 is commanded through the keyboard 45 or the mouse 46 to operate the signal generator 27 to apply the stimulus signal of constant current to the stimulating electrodes 14. The resulting voltages on the sensing electrodes 15 are simultaneously read by the microprocessor 28, which in turn computes the transverse cross-sectional areas of the balloon 10 adjacent the respective sensing electrodes 15. The microprocessor 28 then determines the approximate external longitudinal profile of the inflated balloon 10 from the computed values of the transverse cross-sectional areas of the balloon 10 adjacent the sensing electrodes 15, and produces a signal indicative of the graphical representation 36 of the approximate external longitudinal profile of the balloon 10 which is outputted to the visual display screen 35, and the graphical representation 36 of the external longitudinal profile is displayed on the visual display screen 35, see FIG. 3. If the representation 36 of the external longitudinal profile of the inflated balloon 10 displayed on the visual display screen 35 is not representative of the pouch 2 created in the stomach 3 of the subject during bariatric surgery, the balloon 10 is partially deflated and the balloon catheter 5 is manoeuvred within the pouch 2 and stomach 3 until the balloon 10 extends from the pouch 2 into the upper portion 9 of the stomach 3.

With the balloon catheter 5 and the balloon 10 appropriately located, the balloon 10 is again inflated with the saline solution and the pressure sensor 33 is monitored for determining when the balloon 10 defines the interior of the pouch 2. On the balloon 10 being determined as defining the pouch 2, the microprocessor 28 is commanded to operate the signal generator 27 for applying the stimulus signal of constant current to the stimulating electrodes 14. The microprocessor 28 simultaneously reads the resulting voltage signals on the sensing electrodes 15, and computes the transverse cross-sectional area of the balloon 10 at each of the sensing electrodes 15, and in turn the approximate external longitudinal profile of the balloon 10. The graphical representation 36 of the approximate external longitudinal profile of the balloon 10 is displayed on the visual display screen 35.

Under the control of the microprocessor 28 the transverse lines 39 which represent the locations of the sensing electrodes 15 relative to the graphical representation 36 of the approximate external longitudinal profile of the inflated balloon 10 are displayed on the visual display screen 35 superimposed on the graphical representation 36. The microprocessor 28 computes the derivative of the curved lines 37 of the approximate external longitudinal profile of the inflated balloon 10, from which the points of inflection on the curved lines 37 are determined, for in turn determining the locations 43 and 44 of the points on the curved lines 37 of the approximate external longitudinal profile which correspond to the stoma 4 and the oesophageal sphincter 13. Having determined the locations 43 and 44, the microprocessor 28 outputs signals indicative of the transverse cross-sectional areas of the balloon 10 at the locations 43 and 44. The values of the transverse cross-sectional area of the balloon 10 at the locations 43 and 44 are displayed in the windows 41 and 42 on the visual display screen 35 adjacent the corresponding ones of the transverse lines 39 which correspond to the sensing electrodes 15 adjacent the locations 43 and 44 of the balloon 10. Thus, the sensing electrodes 15 which are adjacent locations of the balloon 10 at the locations 43 and 44 of reduced transverse cross-section can readily be identified on the visual display screen 35. The computed values of the transverse cross-sectional area of the balloon 10 at locations corresponding to all the sensing electrodes 15 are displayed in the windows 38.

The microprocessor 28 computes the volume of the pouch 2 between the locations 43 and 44 which correspond to the stoma 4 and the oesophageal sphincter 13, which corresponds to the volume of the pouch 2, and the computed volume is displayed on the visual display screen 35 in the window 40.

Alternatively, a user through either the keyboard 45 or the mouse 46 selects the transverse lines 39 on the visual display screen 35 which correspond to the sensing electrodes 15 which correspond to the locations 43 and 44 of the balloon 10 of reduced transverse cross-section. In this case, the sensing electrodes 15 which correspond to the locations 43 and 44 of the balloon 10 are the sensing electrodes 15*a* and 15*b* which are represented by the transverse lines 39*a* and 39*b*, respectively, on the visual display screen 35, see FIG. 3. The microprocessor 28 computes the volume of the inflated balloon 10 between the sensing electrodes 15*a* and 15*b* represented by the transverse lines 39*a* and 39*b*. The computed volume is displayed in the window 40 on the visual display screen 35. To assist in identifying the sensing electrodes 15 between which the volume of the inflated balloon 10 is to be computed, the transverse lines 39 may be identified by numbering. For example, the transverse lines 39 may be numbered on the visual display screen 35 consecutively from 1 upwards, the transverse line 39 corresponding to the sensing electrode 15 adjacent the distal end 8 of the catheter 6 being assigned the number 1, and so on.

By knowing the volume of the pouch 2 formed in the stomach 3, a user can then determine if the pouch 2 has increased or decreased in volume since the bariatric surgery had been carried out. Additionally, since the values of the transverse cross-sectional areas of the inflated balloon 10 adjacent the locations 43 and 44 of the graphical representation 36 which correspond respectively to the transverse cross-sectional areas of the stoma 4 and the lower oesophageal sphincter 13, a user is able to ascertain if the area of the oesophageal sphincter 13 and the stoma 4 have dilated since the bariatric surgery had been carried out. If the volume of the pouch 2 has increased or decreased, since the bariatric surgery or since the volume had been computed previously, appropriate corrective surgery can be carried out. Additionally, if the transverse cross-sectional area of the balloon at the locations 43 and 44 which correspond to the transverse cross-sectional area of the stoma 4 and the oesophageal sphincter 13, respectively, have dilated since the bariatric surgery or since the transverse cross-sectional areas thereof had been previously computed, appropriate corrective surgery can be carried out.

Figure 5:
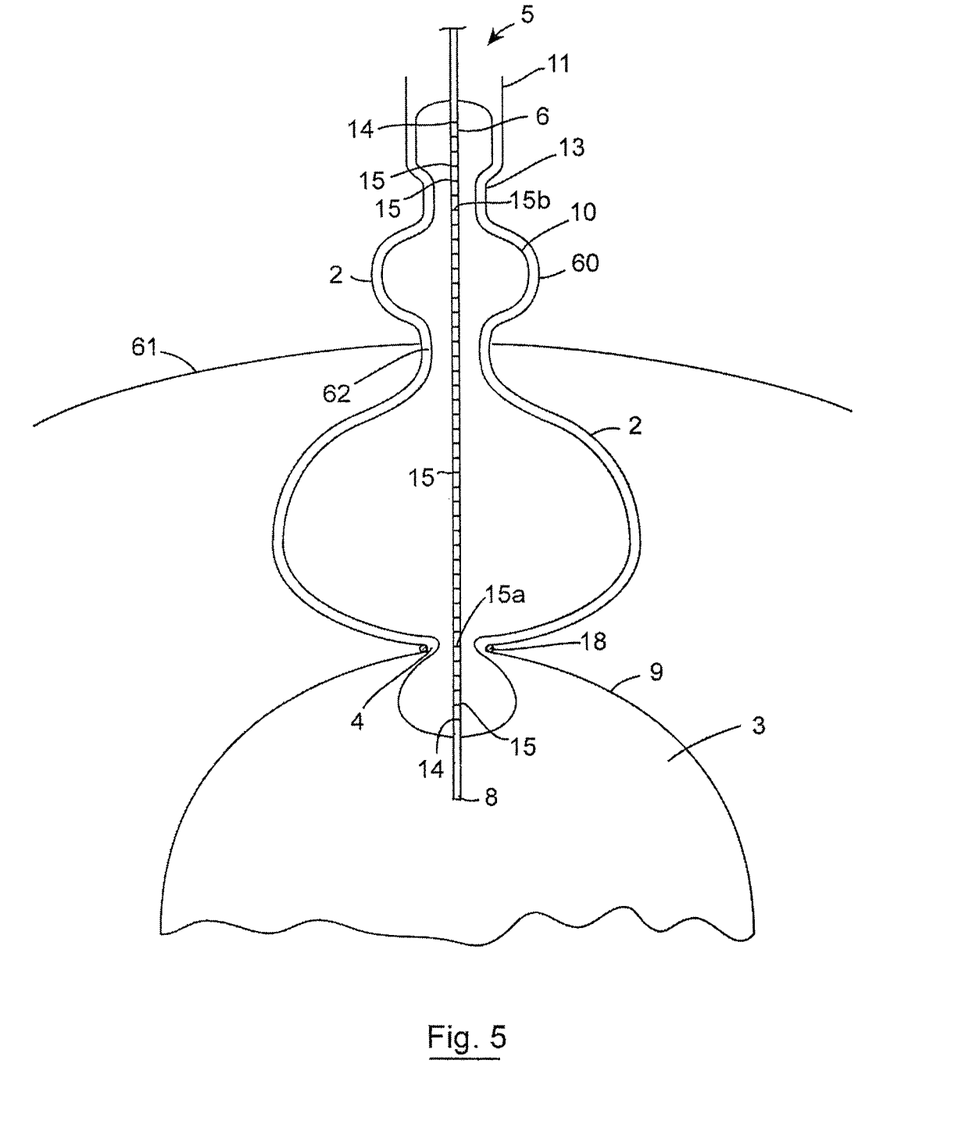
FIG. 5 is another transverse cross-sectional side elevational view of the apparatus of FIG. 1 in use.
Figure 6:
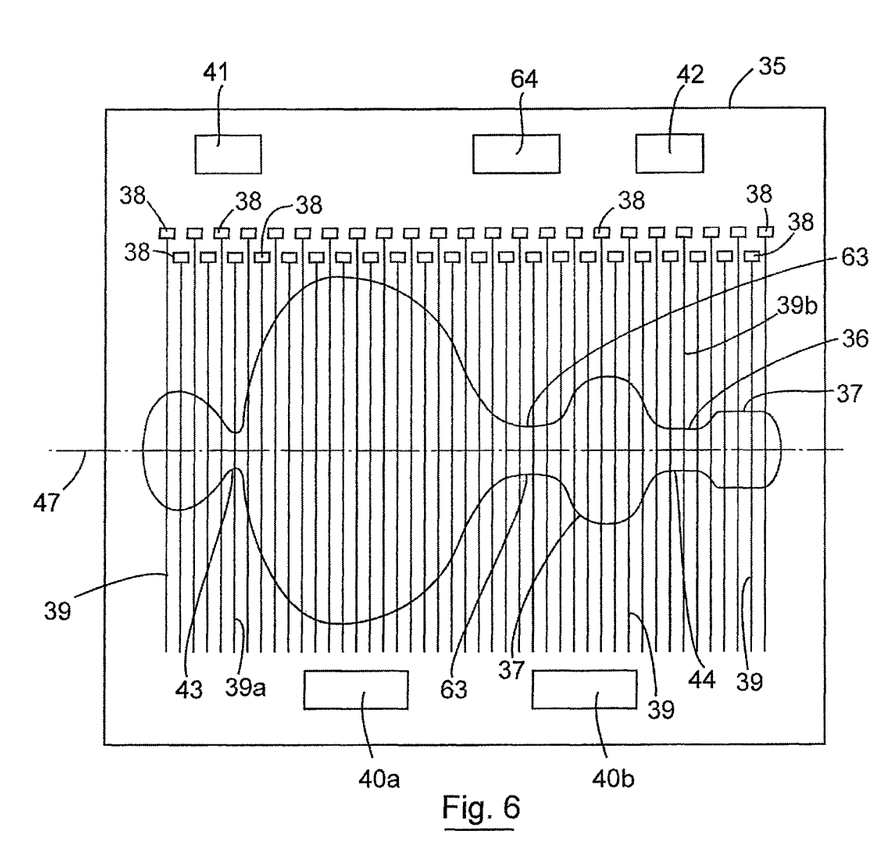
FIG. 6 is a graphical representation of an external longitudinal profile produced by the apparatus of FIG. 1 when used as illustrated in FIG. 5.

Referring now to FIGS. 5 and 6, use of the apparatus 1 for determining the volume of a pouch 2 of the stomach 3 after bariatric surgery is also illustrated. However, in this case a hiatal hernia has occurred, and a portion 60 of the pouch 2 has extended upwardly above the diaphragm 61 of the subject. Pressure of the diaphragm 61 on the pouch 2 results in an intermediate location 62 of reduced transverse cross-section, which is represented on the approximate external longitudinal profile of the balloon 10 displayed on the visual display screen 35 by two intermediate points of inflection 63. Thus, a user by viewing a graphical representation of the approximate external longitudinal profile of the balloon 10 on the visual display screen 35 can readily identify the existence of the hiatal hernia. If desired, the volume of the portion 60 of the pouch 2 between the oesophageal sphincter 13 and the intermediate location 62 adjacent the diaphragm 61 can be determined by selecting the appropriate sensing electrodes 15 which are adjacent the locations 44 and 63 on the graphical representation 36, and within which the part of the inflated balloon 10 which corresponds to the portion 60 of the pouch 2 lies. The volume of the pouch 2 between the diaphragm 61 and the stoma 4 can likewise be determined by selecting the appropriate sensing electrodes 15 which are adjacent the locations 43 and 63. In this case the microprocessor 28 outputs signals indicative of the transverse cross-sectional area of the inflated balloon 10 at the locations 43, 44 and 63 which are displayed in the windows 41 and 42 and in a window 64, respectively, of the visual display screen 35. The volume of the portion of the pouch 2 between the locations 43 and 63 is displayed in the window 40*a*, and the volume of the portion 60 of the pouch 2 is displayed in the window 40*b* of the visual display screen.

Figure 7:
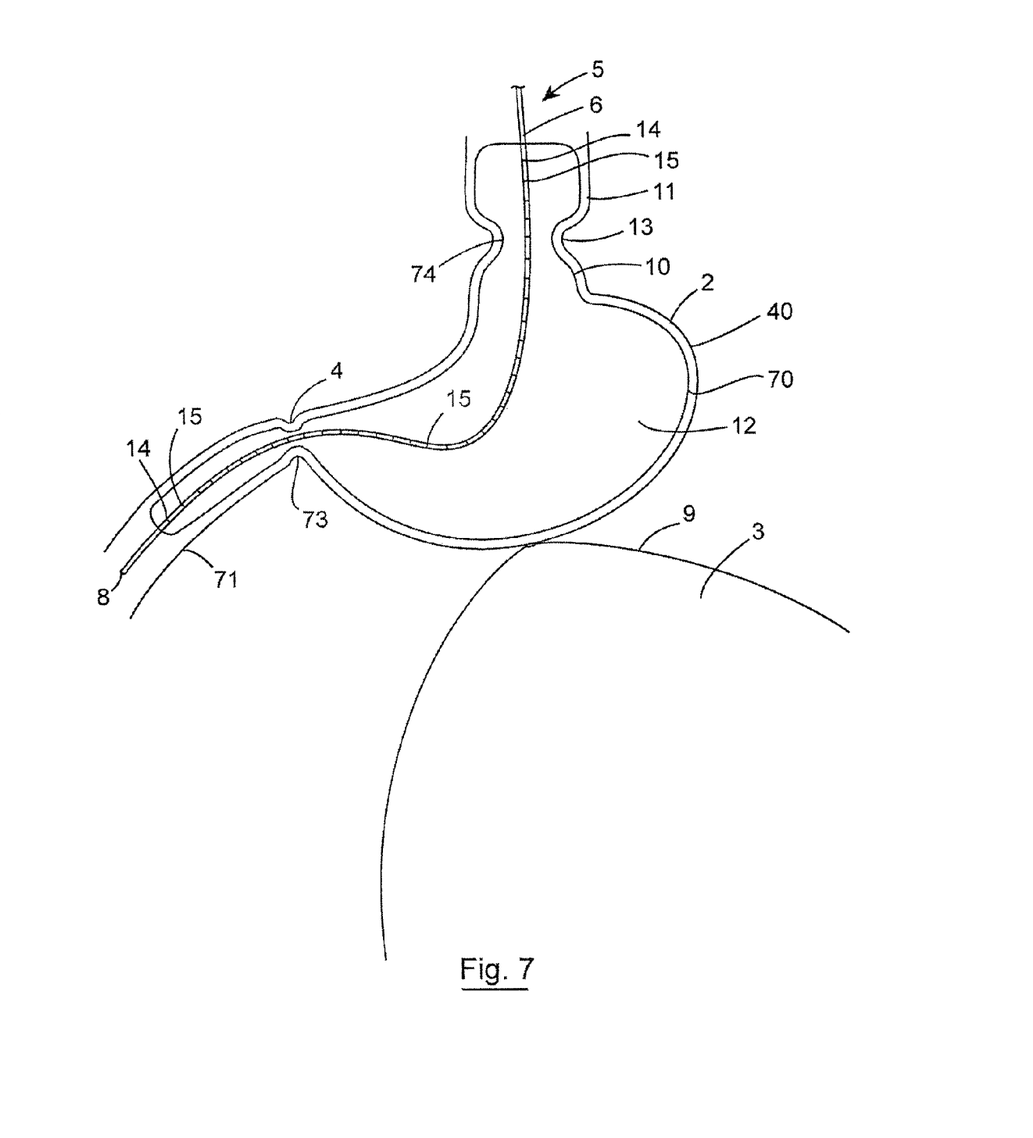
FIG. 7 is a further transverse cross-sectional side elevational view of the apparatus of FIG. 1 in use.
Figure 8:
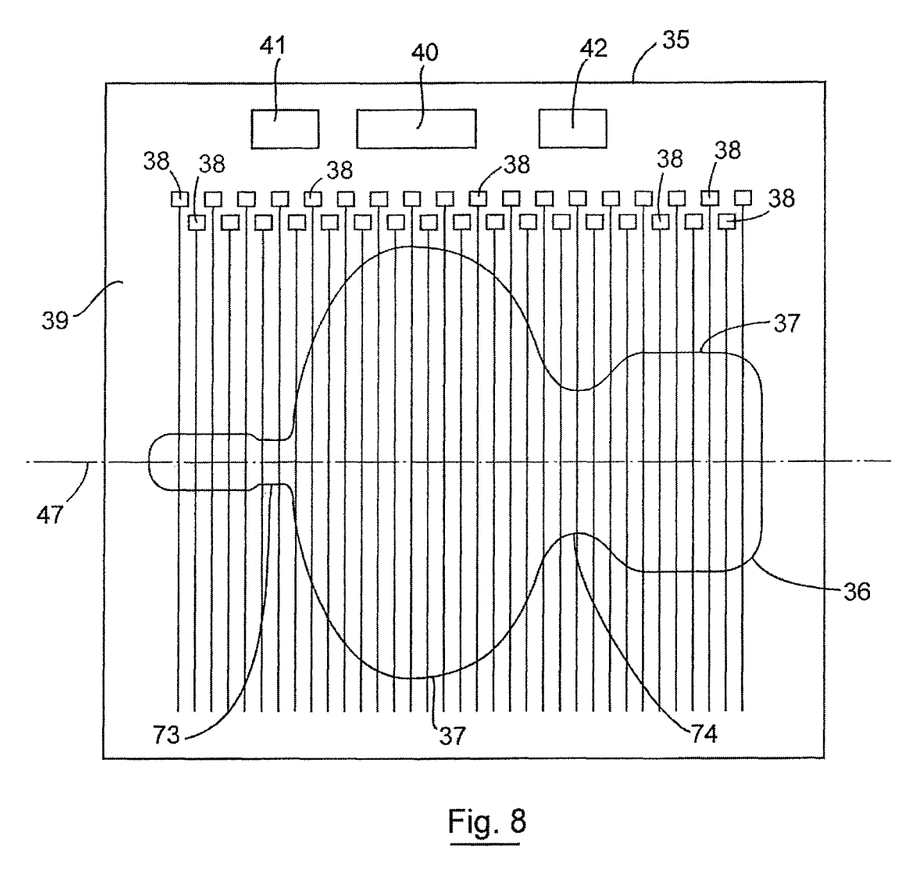
FIG. 8 is a graphical representation of an external longitudinal profile produced by the apparatus of FIG. 1 when used as illustrated in FIG. 7.

In FIGS. 7 and 8 the apparatus 1 is illustrated for determining the volume of a portion 70 of the stomach 3 which has been formed into a pouch 2 during a gastric bypass procedure, and which has been directly coupled to the small intestine 71. Use of the apparatus 1 for determining the volume of the pouch 2 of the stomach 3 in this case is similar to that already described with reference to FIGS. 3 to 6. In this case the balloon catheter 6 is inserted trans-nasally or trans-orally into the oesophagus 11 and through the oesophageal sphincter 13 into the pouch 2, until the distal end 8 of the catheter 6 and a distal portion of the balloon 10 extend through the stoma 4 of the pouch 2 and into the small intestine 71. The balloon 10 is then inflated until it defines the transverse cross-section of the pouch 2. The microprocessor 28 is then operated to operate the signal generator 27 to apply the stimulus signal of constant current to the stimulating electrodes 14, and to simultaneously read the resulting voltage signals on the sensing electrodes 15.

As already described, the microprocessor 28 computes the transverse cross-sectional area of the inflated balloon 10 adjacent the respective sensing electrodes 15, and computes an approximate external longitudinal profile of the inflated balloon 10 based on the computed transverse cross-sectional areas thereof at the respective sensing electrodes 15. However, in this case since the pouch 2 is not symmetrical around a longitudinally extending central axis, the approximate external longitudinal profile of the inflated balloon computed by the microprocessor 28 will not be an exact representation of the actual external longitudinal profile of the balloon or the pouch 2. However, the sensing electrodes 15 which are identified as corresponding to locations of the balloon 10 of reduced transverse cross-section will in fact correspond to the actual locations of reduced transverse cross-section, namely, the locations 73 and 74 which correspond to the stoma 4 and the oesophageal sphincter 13, respectively.

Additionally, the computed values of the transverse cross-sectional area of the balloon 10 at the locations 73 and 74 will be a relatively accurate computation of the actual transverse cross-sectional area of the balloon 10 at the locations 73 and 74, since as discussed above, the transverse cross-sectional area computed by the microprocessor 24 is computed independently of the shape of the balloon. Thus, all the computed values of the transverse cross-sectional area of the balloon 10 adjacent locations corresponding to the sensing electrodes 35 will be relatively accurate values of the respective actual transverse cross-sectional areas. Similarly, since the volume of the balloon between the locations 73 and 74, or any other selected location, which is computed by the microprocessor 28 is computed as a function of the computed transverse cross-sectional areas of the balloon 10 adjacent the corresponding sensing electrodes 15 between the locations 73 and 74 or other selected locations, and is thus independent of the shape of the balloon, the computed volume of the balloon or part thereof is a relatively accurate value of the actual volume of the balloon 10 or part thereof.

To obtain the volume of the pouch 2 between the oesophageal sphincter 13 and the stoma 4, a user selects the two electrodes of the stimulating and sensing electrodes 14 and 15 which correspond to the locations 73 and 74, and inputs the identities of the two electrodes to the microprocessor 28 through the keyboard 45 or the mouse 46. The microprocessor 28 then computes the volume of the inflated balloon 10 between the selected two electrodes, which is equal to the volume of the inflated balloon 10 between the locations 73 and 74 and in turn the pouch 2 between the oesophageal sphincter 13 and the stoma 4. The computed volume is displayed on the visual display screen 35 in the window 40. The transverse cross-sectional area of the inflated balloon 10 adjacent the locations 73 and 74 which correspond to the stoma 4 and the oesophageal sphincter 13, respectively, are also displayed in the windows 41 and 42 of the visual display screen 10. The computed transverse cross-sectional areas of the balloon 10 adjacent the respective sensing electrodes 15 are displayed in the windows 38 in the visual display screen 35. Thus, a user can compare the volume of the pouch 2 and the transverse cross-sectional area of the oesophageal sphincter 13 and the stoma 4 with previously computed values as already described with reference to FIGS. 3 and 6.

Figure 9:
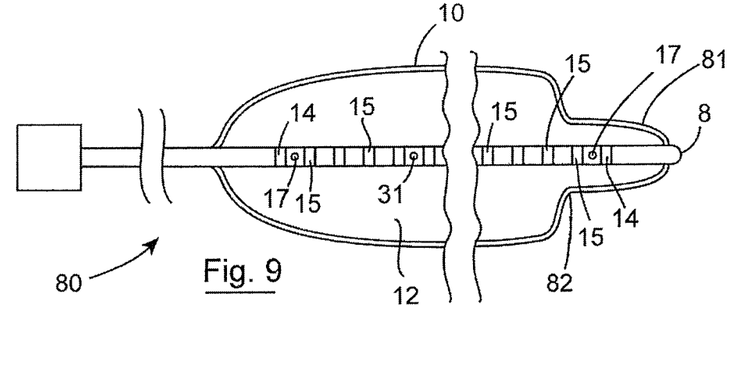
FIG. 9 is a transverse cross-sectional side elevational view of a balloon catheter also according to the invention for use with the apparatus of FIG. 1.

Referring now to FIG. 9, there is illustrated a balloon catheter also according to the invention, indicated generally by the reference numeral 80. The balloon catheter 80 according to this embodiment of the invention is also suitable for use in the apparatus according to the invention described with reference to FIGS. 1 to 4. The balloon catheter 80 is substantially similar to the balloon catheter 6 of the apparatus 1 described with reference to FIGS. 1 to 4, and similar components are identified by the same reference numerals. The only difference between the balloon catheter 80 and the balloon catheter 1 is that a distal portion 81 of the balloon 10 of the balloon catheter 80 is shaped to avoid or minimise dilation of the vessel adjacent a location of reduced transverse cross-section of the pouch 2, in other words, to avoid dilation of the stoma 4 of the pouch 2 during inflating of the balloon 10. In this embodiment of the invention the distal portion 81 of the balloon 10 is of diameter less than the diameter of the remainder of the balloon 10. Otherwise, the balloon catheter 80 is similar to the balloon catheter 6 and its use is likewise similar, with the exception that when the balloon catheter 80 is being inserted into the pouch 2, a portion 82 of the balloon 10 between the distal portion 81 thereof and the remainder of the balloon 10 is located in the stoma 4.

While the apparatus 1 and the method according to the invention have been described for determining the volume of a pouch of a stomach formed as a result of bariatric surgery or a gastric bypass procedure, the apparatus and the method according to the invention may be used for determining the volume of any biological organ or any other vessel, biological or otherwise. Additionally, the apparatus and method according to the invention may be used for determining the volume of any vessel which does not form part of the human or animal body.

In the embodiments of the invention described, the points of inflection along the external longitudinal profile of the balloon have been identified based on the slope of the curved lines 37 which are representative of the external longitudinal profile of the balloon. However, it is envisaged that the points of inflection could be determined by comparing the computed transverse cross-sectional areas with each other.

While the sensing electrodes have been described as being equi-spaced apart from each other, it will be readily apparent to those skilled in the art that the spacing between the sensing electrodes may vary between adjacent pairs of sensing electrodes. It will also be appreciated that the spacing between the stimulating electrodes and the adjacent sensing electrodes may also vary, and may be similar to or different from the spacing between the sensing electrodes. Additionally, while the stimulating and sensing electrodes have been described as being band type electrodes which extend completely around the catheter, it is envisaged in certain cases that the electrodes need not necessarily extend completely around the catheter, and furthermore, electrodes other than band type electrodes may be provided. Indeed, it is also envisaged in certain cases that instead of providing the stimulating and sensing electrodes on the catheter, the stimulating and sensing electrodes may be located on the inner surface of the balloon. Further, it is envisaged that in certain cases the stimulating electrodes may be located on one of the catheter and the inner surface of the balloon, and the stimulating electrodes may be located on the other of the catheter and the inner surface of the balloon.

It is also envisaged that in certain cases a single stimulating electrode may be sufficient. It will be appreciated that any number of sensing electrodes may be provided, and the number of sensing electrodes will be determined by the axial length of the balloon and the resolution of the approximate external longitudinal profile of the balloon required.

While the electrically conductive inflating medium for inflating the balloon has been described as being a saline solution, which is an incompressible fluid, in certain cases, it is envisaged that an electrically conductive compressible fluid may be used, for example, an electrically conductive gaseous medium. However, in which case, when a determination as to when the balloon has been inflated to a state where it defines the interior of the vessel within which it is located is being made based on an increase in the rate of change of pressure of the inflating medium in the balloon per unit mass of the inflating medium delivered into the balloon, this ratio would have to be based on the mass of the inflating medium being delivered into the balloon, when the inflating medium is a compressible medium.

Needless to say, any other compressible or incompressible electrically conductive media may be used for inflating the balloon.

While the apparatus and the method have been described for determining the volume of all or part of a pouch formed in a stomach as a result of bariatric surgery, it will be readily apparent to those skilled in the art that the apparatus and method according to the invention may be used for determining the volume or part of the volume of any compliant vessel in an animal or human body, such as the oesophagus, the stomach or any other vessel.

It is also envisaged that the volume of the vessel or the pouch may be graphically displayed, for example, in the form of an approximate three-dimensional representation.

It is envisaged that in certain cases it may be possible to determine when the inflated balloon defines the interior of the vessel or pouch by detecting a sudden increase in the pressure of the inflating medium during inflating of the balloon.

While in the embodiments of the invention described, the pressure sensor has been located externally of the balloon, and communicates with the balloon through a third lumen, in certain cases, it is envisaged that a pressure sensor may be located within the balloon, and may be located on the catheter within the balloon for monitoring the pressure of the inflating medium in the balloon. In which case, the pressure sensor would be electrically connected to the microprocessor 28 and/or a pressure gauge for indicating the pressure of the inflating medium within the balloon. This, thus, would avoid the need for providing a third lumen through the catheter.

While the balloon catheter of FIG. 9 has been described as comprising a balloon which is shaped adjacent its distal end in order to minimise dilation of the vessel adjacent the one of the locations of reduced transverse cross-section during expansion of the balloon, it is envisaged that instead of shaping the distal end, the proximal end of the balloon could be similarly shaped. Indeed, any other suitable shaping arrangement of either the distal or proximal end of the balloon may be used. It is also envisaged that where the length of the pouch or other vessel is known, and thus, in the case of a pouch the distance between the stoma and the oesophageal sphincter would be known, the balloon could be shaped at both its proximal and distal ends to avoid or to minimise dilation of the stoma and the oesophageal sphincter during inflating of the balloon.

The invention claimed is:

1. A method for determining the volume of a pouch formed in a stomach by bariatric surgery between the lower oesophageal sphincter and a stoma formed in the stomach spaced apart from the lower oesophageal sphincter, the method comprising:

providing an elongated catheter which extends between a proximal end and a distal end and which comprises an inflatable balloon located adjacent the distal end thereof with the catheter extending through the balloon so that on inflating of the balloon the balloon defines with the catheter an annular hollow interior region, the balloon being adapted to define the interior of a part of the stomach comprising the pouch on inflating of the balloon therein, providing at least one stimulating electrode on one of the catheter and the balloon within the balloon, providing a plurality of longitudinally spaced apart sensing electrodes on one of the catheter and the balloon within the balloon longitudinally spaced apart from the at least one stimulating electrode, inserting orally or nasally the distal end of the catheter and the balloon into the part of the stomach comprising the pouch, inflating the balloon with an electrically conductive inflating medium until the balloon defines the interior of the part of the stomach comprising the pouch, applying an electrical stimulus signal to the at least one stimulating electrode, reading signals from the sensing electrodes in response to the stimulus signal, processing the signals read from the sensing electrodes to produce signals indicative of a graphical representation of an approximate external longitudinal profile of the inflated balloon, producing signals indicative of the locations of the respective sensing electrodes relative to the graphical representation of the approximate external longitudinal profile of the inflated balloon, selecting two sensing electrodes at respective axially spaced apart locations along the graphical representation of the approximate external longitudinal profile of the inflated balloon at which the transverse cross-section thereof is of reduced transverse cross-section corresponding respectively to the location of the oesophageal sphincter and the stoma, and computing the volume of the inflated balloon between the two selected axially spaced apart sensing electrodes corresponding to the locations of the lower oesophageal sphincter and the stoma from the signals read from the sensing electrodes.

2. A method as claimed in claim 1 in which the graphical representation of the approximate external longitudinal profile of the inflated balloon is displayed on a visual display screen, and the graphical representation of the sensing electrodes is displayed superimposed on the displayed graphical representation of the approximate external longitudinal profile of the inflated balloon, the sensing electrodes between which the volume of the inflated balloon is to be computed being selected from the displayed graphical representation of the approximate external longitudinal profile of the inflated balloon.

3. A method as claimed in claim 2 in which the sensing electrodes are represented in the displayed graphical representation of the approximate external longitudinal profile of the inflated balloon by respective lines extending transversely relative to the displayed graphical representation of the approximate external longitudinal profile of the inflated balloon.

4. A method as claimed in claim 1 in which the slope of the approximate external longitudinal profile of the inflated balloon is computed for determining the locations along the inflated balloon of reduced transverse cross-section.

5. A method as claimed in claim 1 in which the locations of reduced transverse cross-section in the graphical representation of the approximate external longitudinal profile of the inflated balloon are identified from signals read from the sensing electrodes in response to the stimulus signal being applied to the at least one stimulating electrode.

6. A method as claimed in claim 1 in which a signal is produced indicative of the identities of the ones of the sensing electrodes adjacent the locations at which the inflated balloon is of reduced transverse cross-section.

7. A method as claimed in claim 4 in which the locations of reduced transverse cross-section are determined as a function of the slope of the approximate external longitudinal profile of the inflated balloon.

8. A method as claimed in claim 4 in which the transverse cross-sectional area of the balloon at a location intermediate an adjacent pair of the sensing electrodes is computed with reference to the slope of the approximate external longitudinal profile of the balloon intermediate the said adjacent pair of the sensing electrodes.

9. A method as claimed in claim 1 in which the pressure of the inflating medium is monitored during inflating of the balloon to determine when the balloon defines the interior of the pouch.

10. A method as claimed in claim 9 in which the balloon is determined as defining the interior of the pouch in response to an increase in the pressure of the inflating medium in the balloon during delivery thereof into the hollow interior region of the balloon.

* * * * *